US011446460B1

(12) United States Patent
Carver

(10) Patent No.: US 11,446,460 B1
(45) Date of Patent: Sep. 20, 2022

(54) PRESSURE REGULATED AIRWAY ASSIST DEVICE

(71) Applicant: Dechoker LLC, Wheat Ridge, CO (US)

(72) Inventor: Alan R. Carver, Erie, CO (US)

(73) Assignee: Dechoker LLC, Wheat Ridge, CO (US)

( * ) Notice: Subject to any disclaimer, the term of this patent is extended or adjusted under 35 U.S.C. 154(b) by 0 days.

(21) Appl. No.: 17/497,632

(22) Filed: Oct. 8, 2021

(51) Int. Cl.
| *A61B 17/50* | (2006.01) |
| *A61M 16/06* | (2006.01) |
| *A61M 16/00* | (2006.01) |
| *A61M 16/20* | (2006.01) |
| *A61B 17/24* | (2006.01) |
| *A61M 1/00* | (2006.01) |
| *A61M 39/24* | (2006.01) |
| *A61B 17/30* | (2006.01) |

(52) U.S. Cl.
CPC ......... *A61M 16/0616* (2014.02); *A61B 17/50* (2013.01); *A61M 16/0003* (2014.02); *A61M 16/208* (2013.01); *A61B 17/24* (2013.01); *A61B 2017/306* (2013.01); *A61M 1/81* (2021.05); *A61M 2039/2413* (2013.01)

(58) Field of Classification Search
CPC ... A61B 17/24; A61B 17/50; A61B 2017/306; A61M 1/81; A61M 1/67; A61M 1/80; A61M 1/815; A61M 16/208; A61M 2039/242
USPC ....................................................... 606/106
See application file for complete search history.

(56) References Cited

U.S. PATENT DOCUMENTS

| 3,809,079 | A | | 5/1974 | Buttaravoli |
| 3,939,830 | A | * | 2/1976 | da Costa ................. A61M 1/67 |
| | | | | 128/206.29 |
| 4,082,095 | A | | 4/1978 | Mendelson et al. |
| 4,537,189 | A | | 8/1985 | Vicenzi |
| 4,971,053 | A | * | 11/1990 | Tarrats .................... A61B 17/50 |
| | | | | 128/206.28 |
| 5,313,938 | A | | 5/1994 | Garfield et al. |
| 5,338,166 | A | | 8/1994 | Schultz |
| 5,611,376 | A | | 3/1997 | Chuang |
| 5,871,462 | A | * | 2/1999 | Yoder ................. A61B 17/1644 |
| | | | | 83/13 |
| 6,532,956 | B2 | | 3/2003 | Hill |
| 7,387,062 | B2 | | 6/2008 | Chen |
| 9,357,905 | B2 | | 6/2016 | Molnar et al. |
| 10,258,319 | B2 | | 4/2019 | Arden et al. |
| 10,342,526 | B2 | | 7/2019 | Arden et al. |
| 10,675,393 | B1 | | 6/2020 | Carver |
| 2001/0035186 | A1 | | 11/2001 | Hill |
| 2005/0085799 | A1 | | 4/2005 | Luria et al. |
| 2007/0251528 | A1 | | 11/2007 | Seitz |

(Continued)

OTHER PUBLICATIONS

PCT International Patent Application No. PCT/US21/36216, International Search Report and Written Opinion of the International Searching Authority dated Oct. 1, 2021, 14 pages.

(Continued)

*Primary Examiner* — Diane D Yabut
*Assistant Examiner* — Christian D Knauss
(74) *Attorney, Agent, or Firm* — Craig R. Miles; CR Miles P.C.

(57) ABSTRACT

An airway assist device and methods of making and using an airway assist device to assist in opening an airway or removing fluid or material obstructing an airway of a subject.

22 Claims, 14 Drawing Sheets

(56) References Cited

U.S. PATENT DOCUMENTS

| | | | |
|---|---|---|---|
| 2008/0312636 A1* | 12/2008 | Miller | A61B 90/92 604/509 |
| 2009/0175747 A1 | 7/2009 | LeBoeuf et al. | |
| 2009/0228018 A1 | 9/2009 | Winiarski | |
| 2011/0152794 A1 | 6/2011 | Carver | |
| 2012/0221010 A1 | 8/2012 | DeLuca et al. | |
| 2013/0324798 A1 | 12/2013 | Molnar et al. | |
| 2015/0190158 A1 | 7/2015 | Lih | |
| 2017/0000641 A1 | 1/2017 | Arden et al. | |
| 2017/0266401 A1 | 9/2017 | Arden et al. | |
| 2019/0150962 A1 | 5/2019 | Cutino | |
| 2019/0290873 A1 | 9/2019 | Willett | |
| 2020/0306420 A1* | 10/2020 | Carver | A61M 1/962 |
| 2022/0008643 A1 | 1/2022 | Carver | |

OTHER PUBLICATIONS

U.S. Appl. No. 17/484,830, filed Sep. 24, 2021.
Amazon. Dechoker Anti-Choking Device for Adults (Ages 12 Years and up). Website, https://www.amazon.com, review from Oct. 21, 2019, originally downloaded Aug. 10, 2021, 11 pages.
U.S. Appl. No. 12/653,645, filed Dec. 17, 2009.
U.S. Appl. No. 12/928,690, filed Dec. 15, 2010.
U.S. Appl. No. 13/135,783, filed Jul. 15, 2011.
U.S. Appl. No. 13/830,574, filed Mar. 14, 2013.
U.S. Appl. No. 14/794,285, filed Jul. 8, 2015.
U.S. Appl. No. 15/210,944, filed Jul. 15, 2016.
U.S. Appl. No. 15/210,944, Office Action dated Feb. 10, 2017.
U.S. Appl. No. 15/210,944, Office Action dated Sep. 20, 2017.
U.S. Appl. No. 15/210,944, Office Action dated Jan. 12, 2018.
U.S. Appl. No. 15/210,944, Office Action dated Jun. 22, 2018.
U.S. Appl. No. 15/210,944, Office Action dated May 20, 2019.
U.S. Appl. No. 15/210,944, Appeal Brief filed Feb. 21, 2019.
U.S. Appl. No. 16/895,941, filed Jun. 8, 2020.
U.S. Appl. No. 29/741,865, filed Jul. 16, 2020.
U.S. Appl. No. 16/895,941, Office Action dated Oct. 12, 2021.
U.S. Appl. No. 16/895,941, Office Action dated Dec. 6, 2021.
U.S. Appl. No. 17/484,830, Office Action dated Oct. 29, 2021.

* cited by examiner

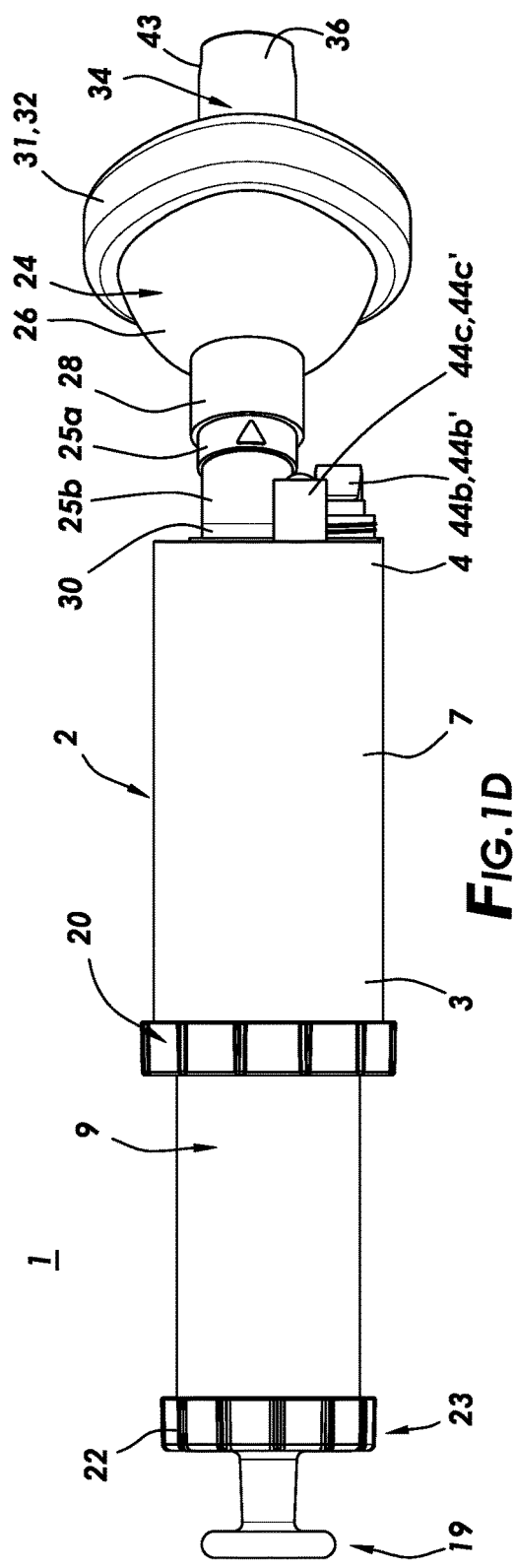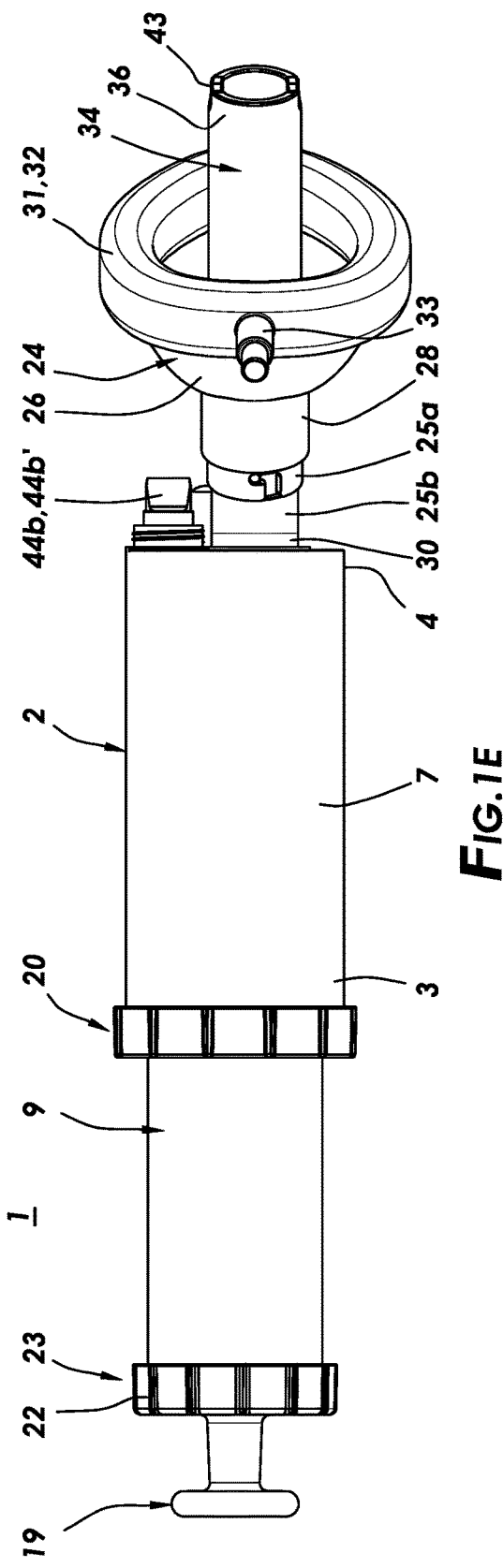

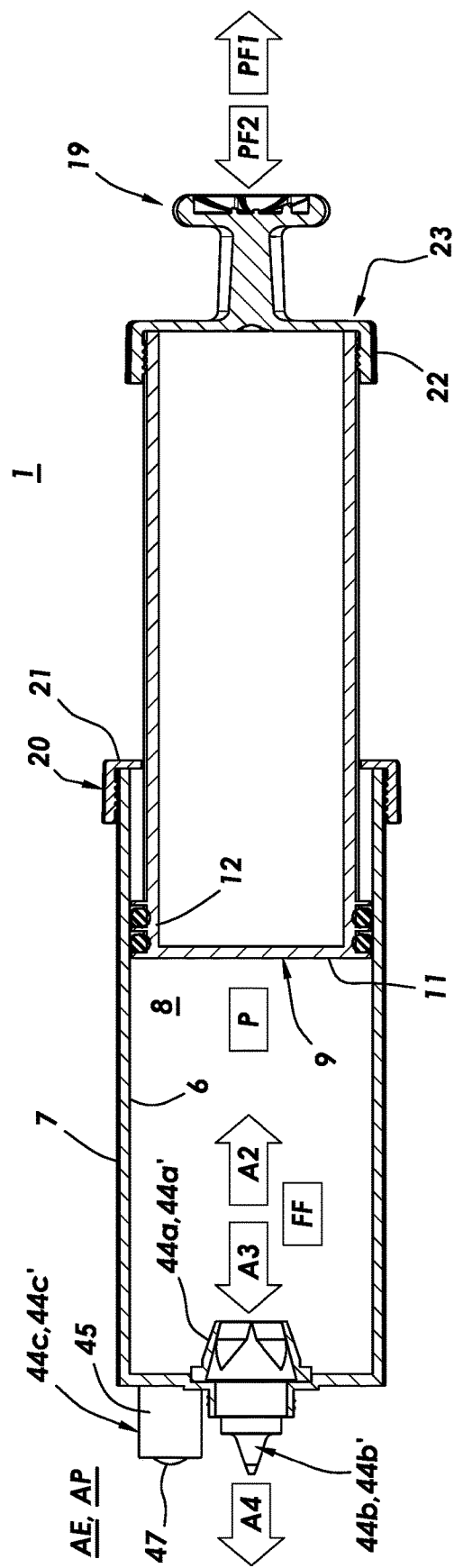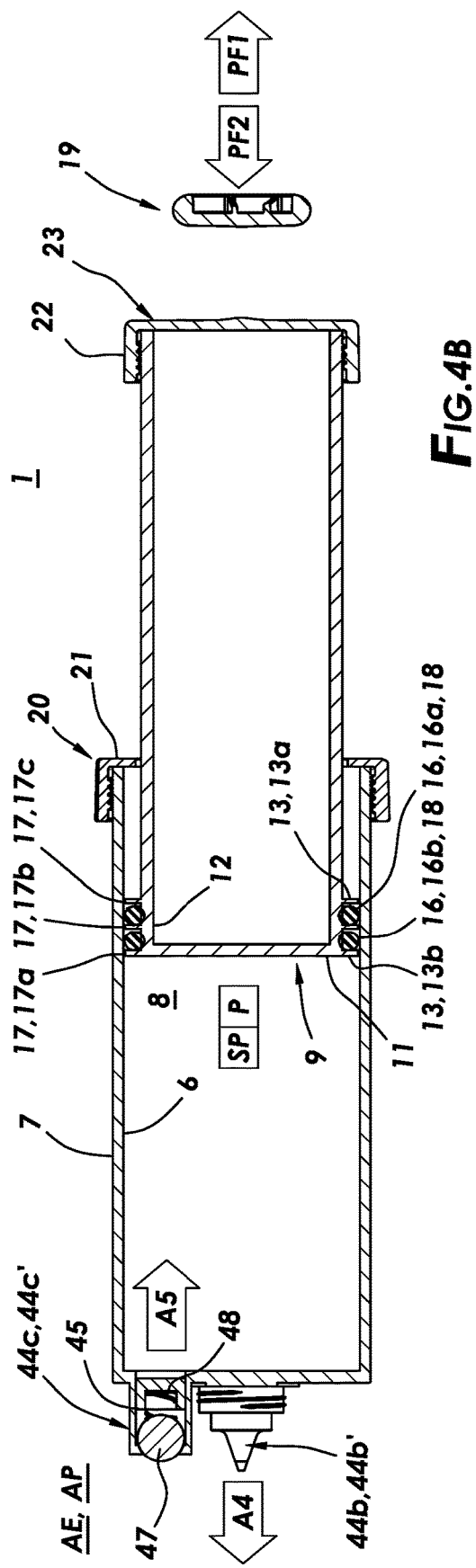

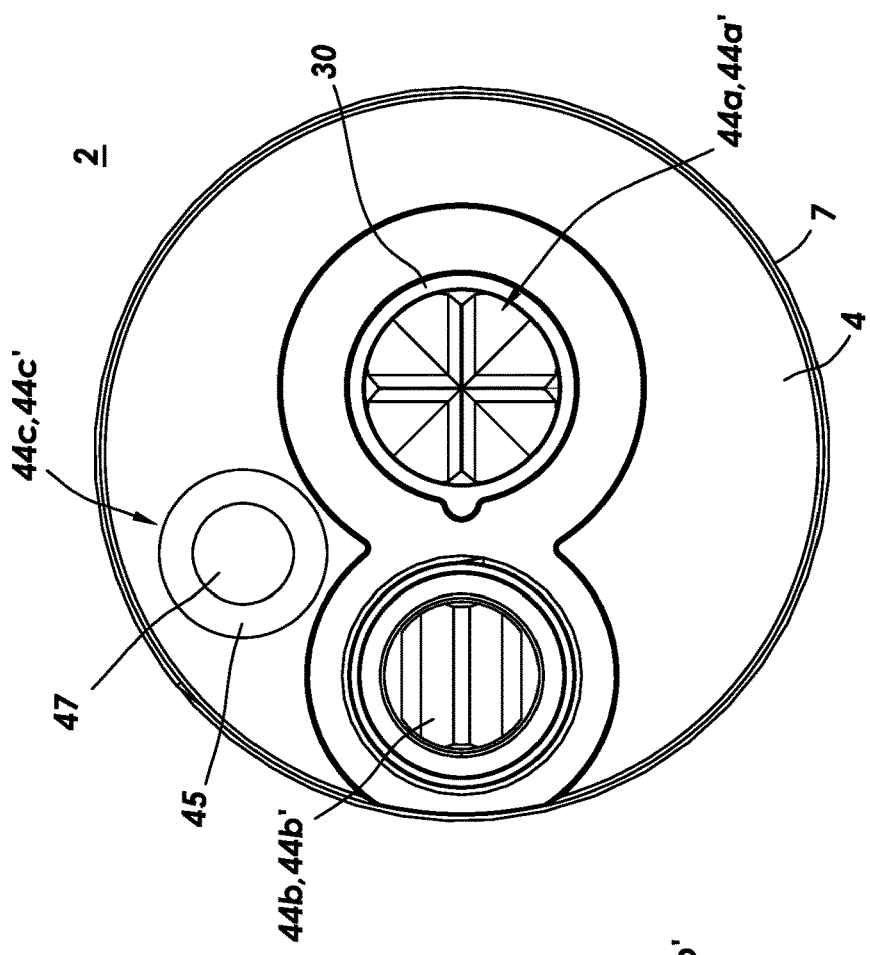
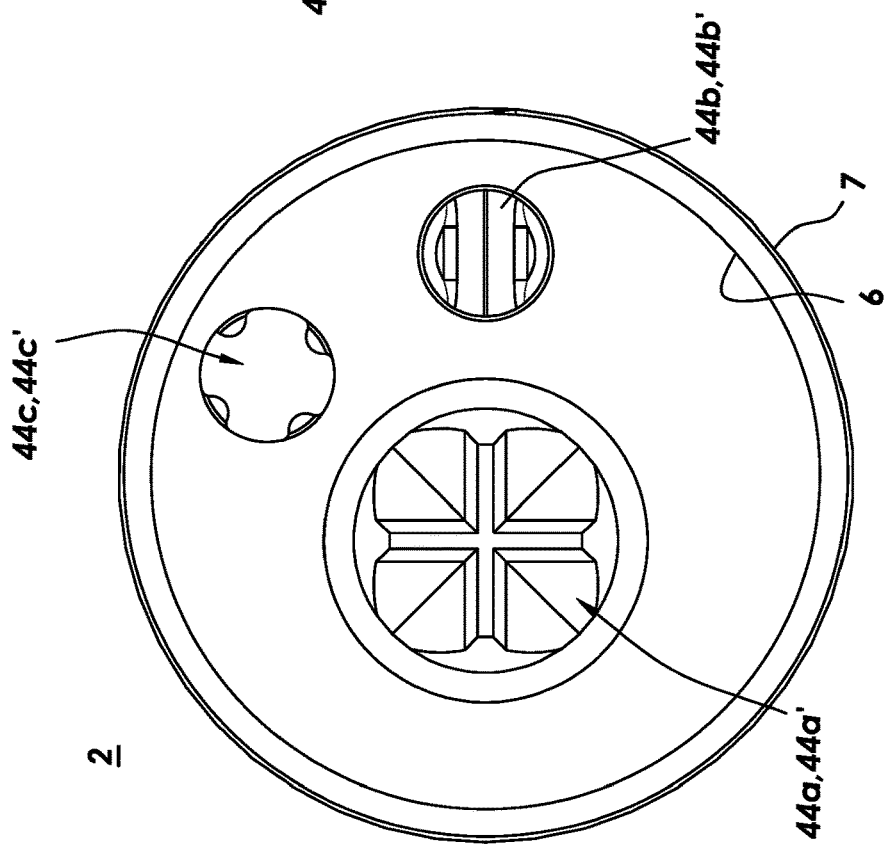

PRESSURE REGULATED AIRWAY ASSIST DEVICE

I. FIELD OF THE INVENTION

An airway assist device and methods of making and using an airway assist device to assist in opening an airway or removing fluid or material obstructing an airway of a subject.

II. BACKGROUND OF THE INVENTION

A drawback to conventional airway assist devices that use suction pressure to assist in dislodging objects in the airway of a subject can be that the suction pressure generated during use of the airway assist device can cause injury to the mouth, nose, throat, or lungs of the subject. Accordingly, there would be a substantial advantage in an airway assist device which regulated the suction pressure in the airway assist device during use within a range that prevents or minimizes injury to the mouth, nose, throat or lungs of a subject.

III. SUMMARY OF THE INVENTION

A broad object of embodiments of the invention can be to provide an airway assist device including a barrel having a barrel proximal end and a barrel distal end having a barrel distal end opening, a plunger slidably disposed within the barrel, a face mask having a hollow stem fluidically coupled to the barrel distal end opening, wherein the face mask has a configuration to seal about a mouth and nose of a person, and a one-way valve configured to regulate suction pressure within the barrel upon outward draw of the plunger toward the barrel proximal end. The suction pressure can be regulated in a suction pressure range to assist in dislodging objects in the airway of a subject while preventing or minimizing injury to the mouth, nose, throat or lungs of a subject.

Naturally, further objects of the invention are disclosed throughout other areas of the specification, drawings, photographs, and claims.

IV. BRIEF DESCRIPTION OF THE DRAWINGS

FIG. 1D is a top plan view of a particular embodiment of the airway assist device.

FIG. 1E is a bottom plan view of a particular embodiment of the airway assist device.

FIG. 4A is a cross section view 4A-4A of the particular embodiment of the airway assist device as shown in FIG. 3.

FIG. 4B is a cross section view 4B-4B of the particular embodiment of the airway assist device as shown in FIG. 3.

FIG. 5C is second end elevation view of the barrel and valve assembly of a particular embodiment of the airway assist device.

FIG. 5D is a first end elevation view of the barrel and valve assembly of a particular embodiment of the airway assist device.

V. DETAILED DESCRIPTION OF THE INVENTION

Figure 1A:
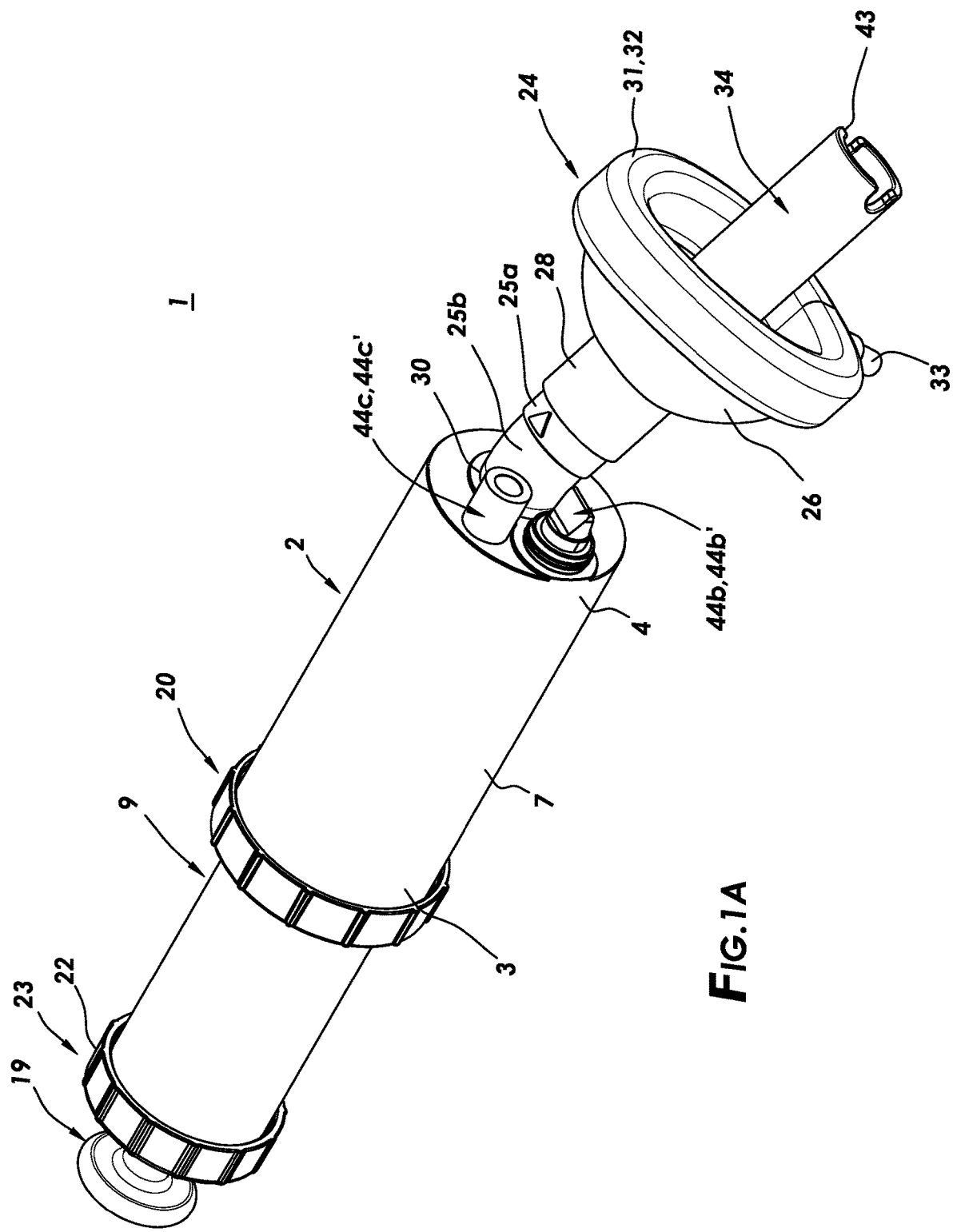
FIG. 1A is a perspective view of a particular embodiment of the airway assist device.
Figure 1B:
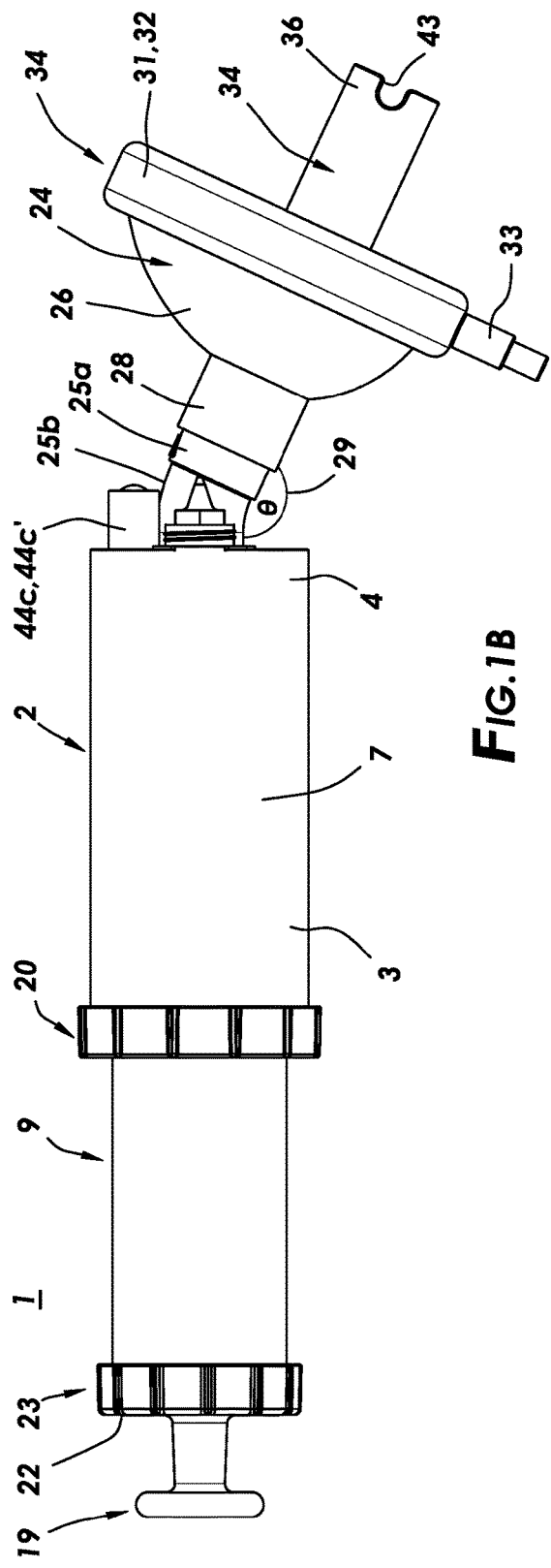
FIG. 1B is a first side elevation view of a particular embodiment of the airway assist device.
Figure 1C:
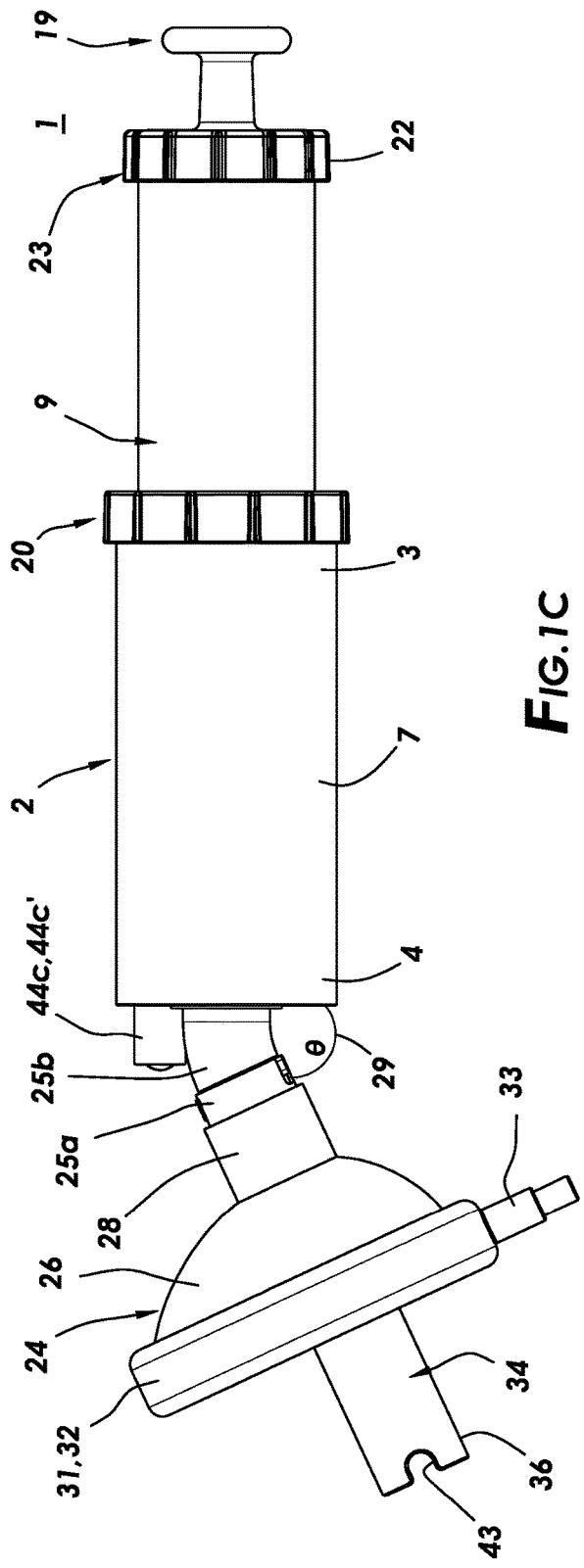
FIG. 1C is a second side elevation view of a particular embodiment of the airway assist device.
Figure 1G:
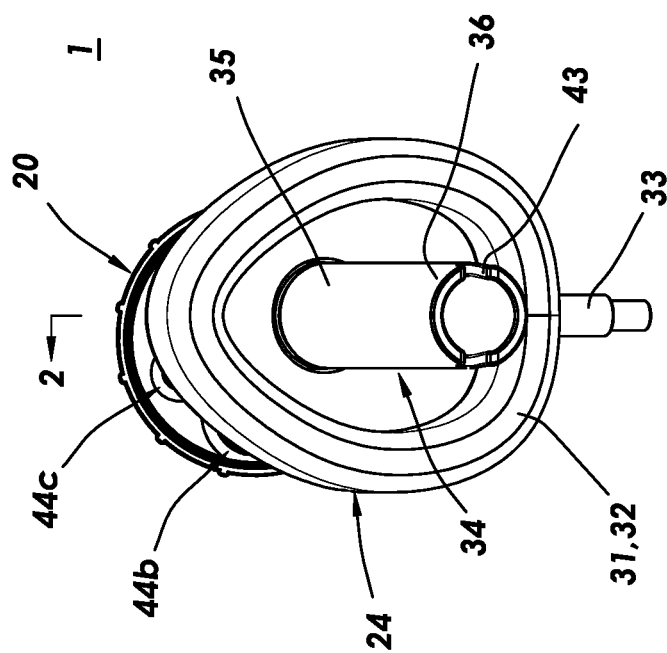
FIG. 1G is a second end elevation view of a particular embodiment of the airway assist device.
Figure 1F:
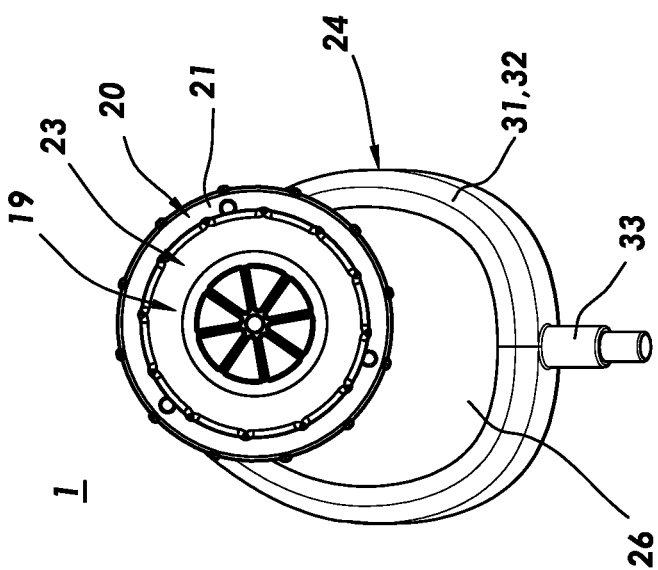
FIG. 1F is a first end elevation view of a particular embodiment of the airway assist device.

Generally, referring to FIGS. 1A-1G, 2-3, 4A-4C, 5A-5D, 6A-6B, and 7-8, particular embodiments of an airway assist device (1), methods of making an airway assist device (1) and methods of using an airway assist device (1) to assist in opening an airway (A) or removing fluid or material (O) obstructing the airway (A) of a subject (S).

Now, with primary reference to 1A-1G, 2-3, 4A-4C, 5A-5D, 6A-6B, and 7, embodiments of the airway assist device (1) can include a barrel (2) having a barrel proximal end (3) and a barrel distal end (4). The barrel proximal end (3) can be an open end. The barrel distal end (4) can be a closed end having a barrel distal end opening (5) which communicates between a barrel internal surface (6) and a barrel external surface (7). The barrel internal surface (7) defines a barrel interior chamber (8). While the Figures depict the barrel (2) as being cylindrical in configuration, this is not intended to preclude other embodiments having different cross-sectional tubular structures including as illustrative examples: an oval, a triangle, a square, a rectangle, a parallelogram, a rhombus, a trapezium, a kite, a polygon including but not necessarily limited to: a pentagon, a hexagon, an octagon, a nonagon, a decagon, and combinations thereof.

Again, with primary reference to 1A-1G, 2-3, 4A-4C, 5A-5D, 6A-6B, and 7A, a plunger (9) can be slidably disposed within the barrel (2). In particular embodiments, the plunger (2) can include a plunger proximal end (10) opposite a plunger distal end (11) joined by a plunger sidewall (12) configured to reciprocally move within the barrel interior chamber (8). In particular embodiments, the plunger sidewall (12) can slidably engage the barrel internal surface (8). In those embodiments in which the plunger (9) engages the barrel internal surface (6), one or more channels (13) can encircle the plunger (9). The one or more channels (13) can take the form of one or more grooves (14) disposed in and encircling the plunger (9). In particular embodiments, the one or more grooves (14) can act to reduce frictional engagement between the plunger sidewall (12) and the barrel internal surface (6) to allow the plunger (9) to slide more freely within the barrel (2). In particular embodiments, the plunger sidewall (12) can be configured to provide an annular space (15) between the plunger sidewall (12) and the barrel internal surface (6) to allow the plunger (9) to move freely in the barrel interior chamber (8). A seal (16) can, but need not necessarily, be disposed in each of the one or more grooves (14) to encircle the plunger sidewall (12). The seal(s) (16) disposed in the one or more grooves (13) can outwardly extend from the plunger sidewall (12) to slidably engage the barrel internal surface (6) bridging the annular space (15).

In particular embodiments, the one or more channels (13) can comprise two or more concentric rings (17) disposed in fixed spatial relation a distance apart and encircling the plunger sidewall (12) to form a channel (13) between each pair of concentric rings (17a, 17b, 17c . . . 17n). In particular embodiments the two or more concentric rings (17a, 17b, 17c . . . 17n) can slidably engage the barrel internal surface (6). In other embodiments, the two or more concentric rings (17a, 17b, 17c . . . 17n) can be configured provide an annular space (15) between the two or more concentric rings (17a, 17b, 17c . . . 17n) and the barrel internal surface (6) to allow the plunger (9) to move freely in the barrel interior chamber (8). A seal (16) can, but need not necessarily, be disposed in each of the one or more channels (13) to encircle the plunger sidewall (12). The seal(s) (16) disposed in the one or more channels (13a, 13b . . . 13n) can outwardly extend from the plunger sidewall (12) to slidably engage the barrel internal surface (6) bridging the annular space (15). As shown the illustrative example of FIG. 2, three concentric rings (17a, 17b, 17c) can be disposed in fixed spaced apart relation on the plunger sidewall (12) to form a first channel (13a) and a second channel (13b). The three concentric rings (17a, 17b, 17c) have a configuration which provide an annular chamber (15) between the three concentric rings (17a, 17b, 17c) and the barrel internal surface (6) to allow the plunger (9) to move freely in the barrel interior chamber (8). A first seal (16a) can be disposed in first channel (13a) encircling the plunger sidewall (12) and a second seal (16b) can be disposed in the second channel (13b) to encircle the plunger sidewall (12). The seal(s) (16a, 16b) can outwardly extend beyond the three concentric rings (17a, 17b, 17c) to slidably engage the barrel internal surface (6) of the barrel (2). In particular embodiments, the one or more seals (16) can, but need not necessarily, be an O-ring (18). An O-ring (18), for the purposes of this invention, comprises a mechanical gasket, typically, but not necessarily, in the shape of a torus including a loop of elastomer with a round cross-section, configured to be seated in a channel (13) and encircling the plunger sidewall (12). The cross-section of the loop of material, while typically round, can take any configuration in cross-section that when seated in the channel (13) can slidably engage the barrel internal surface (6). The O-ring (18) can be compressed between the plunger sidewall (12) and the barrel internal surface (6). As illustrative examples, with primary reference to 1A-1G, 2-3, 4A-4C, 5A-5D, 6A-6B, and 7A can have a cross-section that may be square or rectangular or comprise an encircling band with an extending flattened structure that contacts the barrel internal surface (6).

Again, with primary reference to 1A-1G, 2-3, 4A-4C, 5A-5D, 6A-6B, and 7A, in particular embodiments, a handle (19) can be connected to the plunger (9) and extending outward of the barrel proximal end (3). The handle (19) can be configured in any manner that extends outward of the barrel proximal end (3) and can receive pulling forces (PF1) or pushing forces (PF2) to correspondingly reciprocally move the plunger (9) inside the barrel (2) between the barrel distal end (4) and the barrel proximal end (3). In the illustrative example shown in the Figures, the plunger (9) can comprise a tubular member having a plunger length (PL) disposed between the plunger distal end (11) opposite the plunger proximal end (10) extending outwardly of the barrel proximal end (3). A handle (19) can be attached to plunger proximal end (10). The handle (19) can be configured to be readily grasped by a hand to apply pulling forces (PF1) or pushing forces (PF2) to correspondingly reciprocally move the plunger (9) in the barrel (2). However, the illustrative example of the Figures is not intended to preclude embodiments in which the handle (19) comprises an elongate member having an elongate member first end connected directly to the plunger and an elongate member second end extending outward of the barrel proximal end (3). For example, the elongate member can be a thin straight rod.

Again, with primary reference to 1A-1G, 2-3, 4A-4C, 5A-5D, 6A-6B, and 7A, in particular embodiments, a retainer ring (20) having a radially inwardly extending retainer ring shoulder (21) can be coupled to the barrel proximal end (3). The retainer ring shoulder (21) can radially inwardly extend a distance sufficient to prevent removal of the plunger (9) from the barrel (2). In particular embodiments, the plunger (9) can engage the retainer ring shoulder (21) when drawn toward the barrel proximal end (3). In the illustrative embodiments shown in the Figures, one of the concentric rings (17) disposed on and encircling the plunger (9) can engage the retainer ring shoulder (21) when drawn toward the open barrel proximal end (3) to prevent removal of the plunger (9) from the barrel (2).

In particular embodiments, a portion of the plunger (9) or the handle (19) extending outward of the barrel proximal end (3) can be configured to radially outwardly extend to engage the retaining ring shoulder (21) when the plunger (9) is pushed toward the barrel distal end (4) to prevent the plunger (9) from engaging the barrel distal end (4). In the embodiments shown in the Figures, the plunger proximal end (10) extending outward of the barrel proximal end (3) can have plunger proximal end annular member (22) that outwardly radially extends a sufficient distance to engage the retainer ring shoulder (21) when the plunger (9) moves toward the barrel distal end (4) to prevent the plunger from engaging the barrel distal end (4). In particular embodiments, the retaining ring (20) and the plunger proximal end annular member (22) can correspondingly threadingly couple with the open barrel proximal end (3) and the plunger proximal end (10) which can allow for removal of the retaining ring (20) or the plunger proximal end annular member (22) to allow removal of the plunger (9) from the barrel (2). In particular embodiments, the plunger proximal end annular member (22) can be a part of a plunger cap (23) coupled to the plunger proximal end (10).

In particular embodiments, a face mask (24) can be fluidically coupled to the barrel distal end opening (5) in the barrel distal end (4) directly or through one or more hollow connectors (25). The face mask (24) can include a dome (26) extending to a dome outer periphery (27) which can be configured to engage a subject (S). A hollow stem (28) can outwardly extend from the dome (26) of the face mask (24) and be configured to fixedly couple or removably couple directly or indirectly through one or more hollow connectors (25) to the barrel distal end opening (5) in the barrel distal end (4) of the barrel (2). The hollow stem (28) and the one or more hollow connectors (25) can be straight, or the hollow stem (28) and the one or more hollow connectors (25) can, but need not necessarily, include a non-straight angle (29). A tubular extension (30) can be disposed about the barrel distal end opening (5) in the barrel distal end (4) of the barrel (2). The hollow stem (28) or one or more hollow connectors (25) can be connected to the tubular extension (30). In particular embodiments, a small aperture can be disposed in the face mask (24) to assist in preventing over pressurization of the face mask (24). In particular embodiments, the face mask (24) can, but need not necessarily, include a plurality of face masks (24) which can be of the same size, or can have a range of different sizes to correspondingly engage a plurality of subjects (S) of different sizes. Accordingly, a plurality of face masks (24) can be interchangeably fluidically coupled to the barrel (2) for the purposes of replacement of lost or damaged face masks (24), maintain sterile conditions, or to fit the features or size of each of a plurality of subjects (S). In particular embodiments, the dome outer periphery (27) can, but need not necessarily, engage an annular cuff (31). The annular cuff (31) can comprise a solid material having a density, hardness, or compression, or combination thereof, to conform to the subject's face (F) about the mouth (M) and nose (N) as shown in the illustrative example of FIG. 8.

Figure 2:
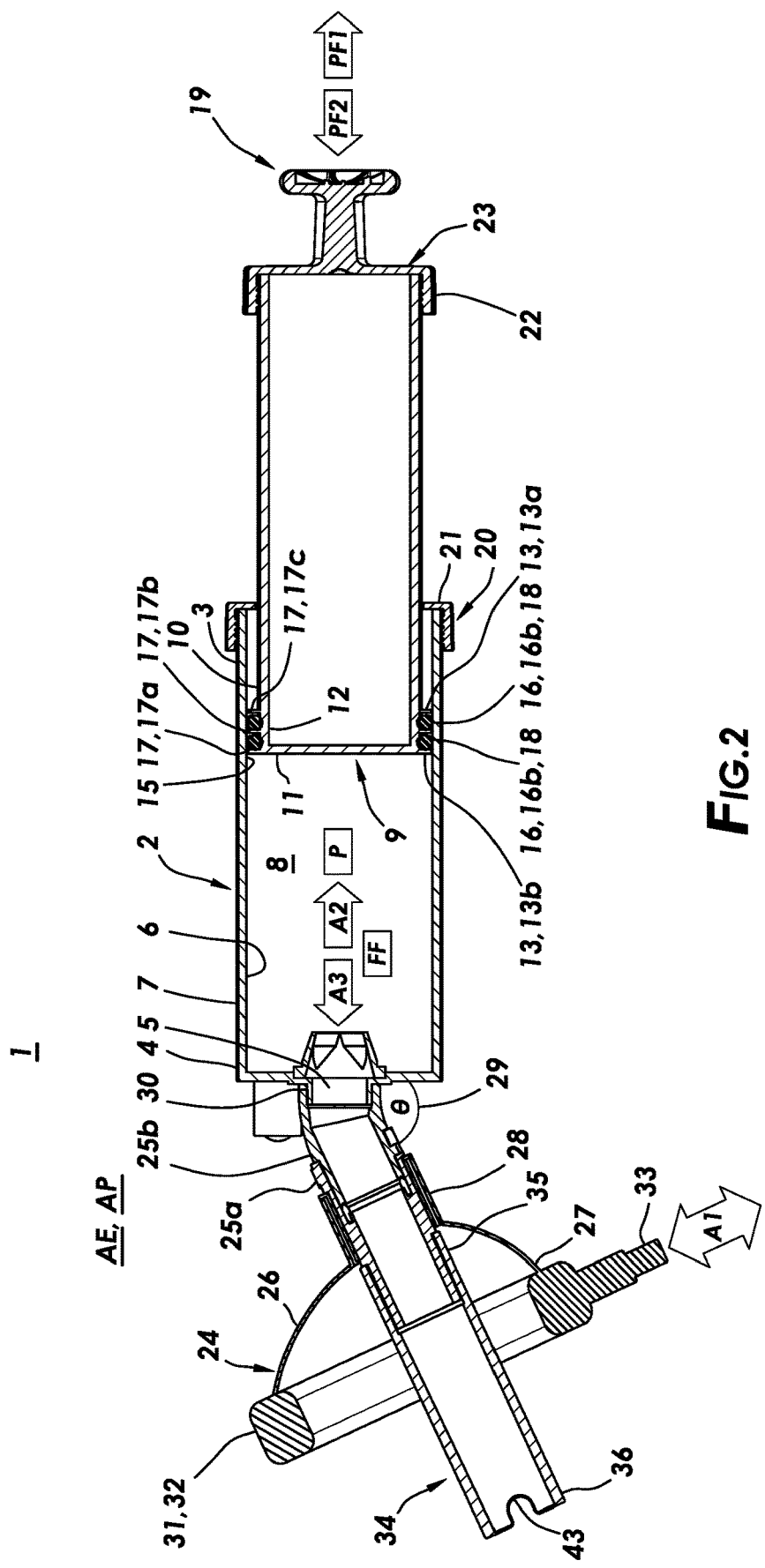
FIG. 2 is a cross section view 2-2 of the particular embodiment of the airway assist device shown in FIG. 1D.
Figure 7:
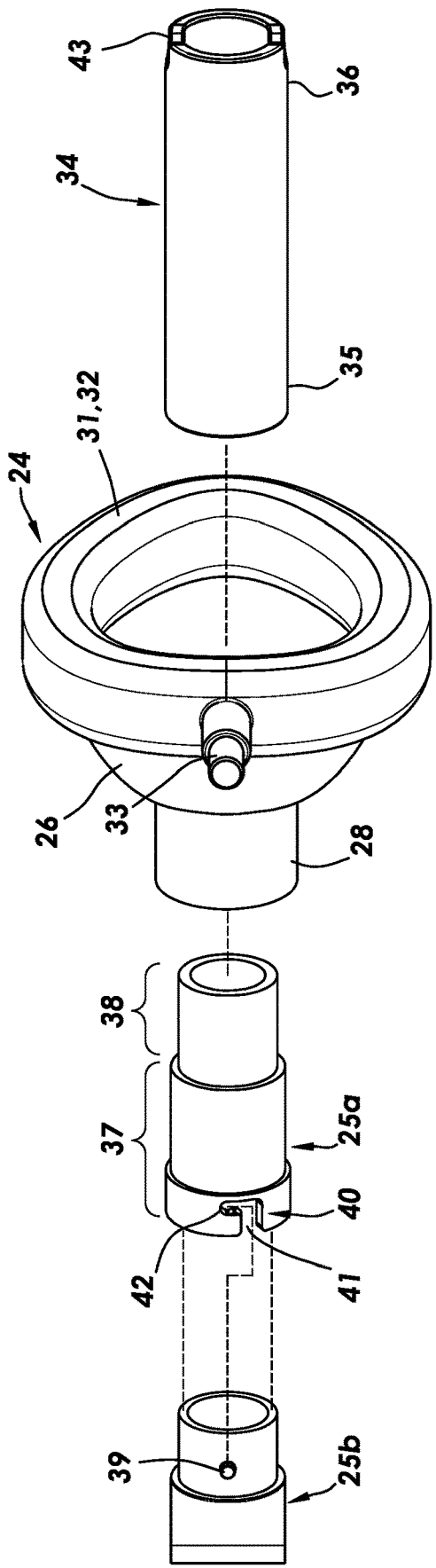
FIG. 7 is an exploded bottom plan view of a face mask assembly of a particular embodiment of the airway assist device.
Figure 8:
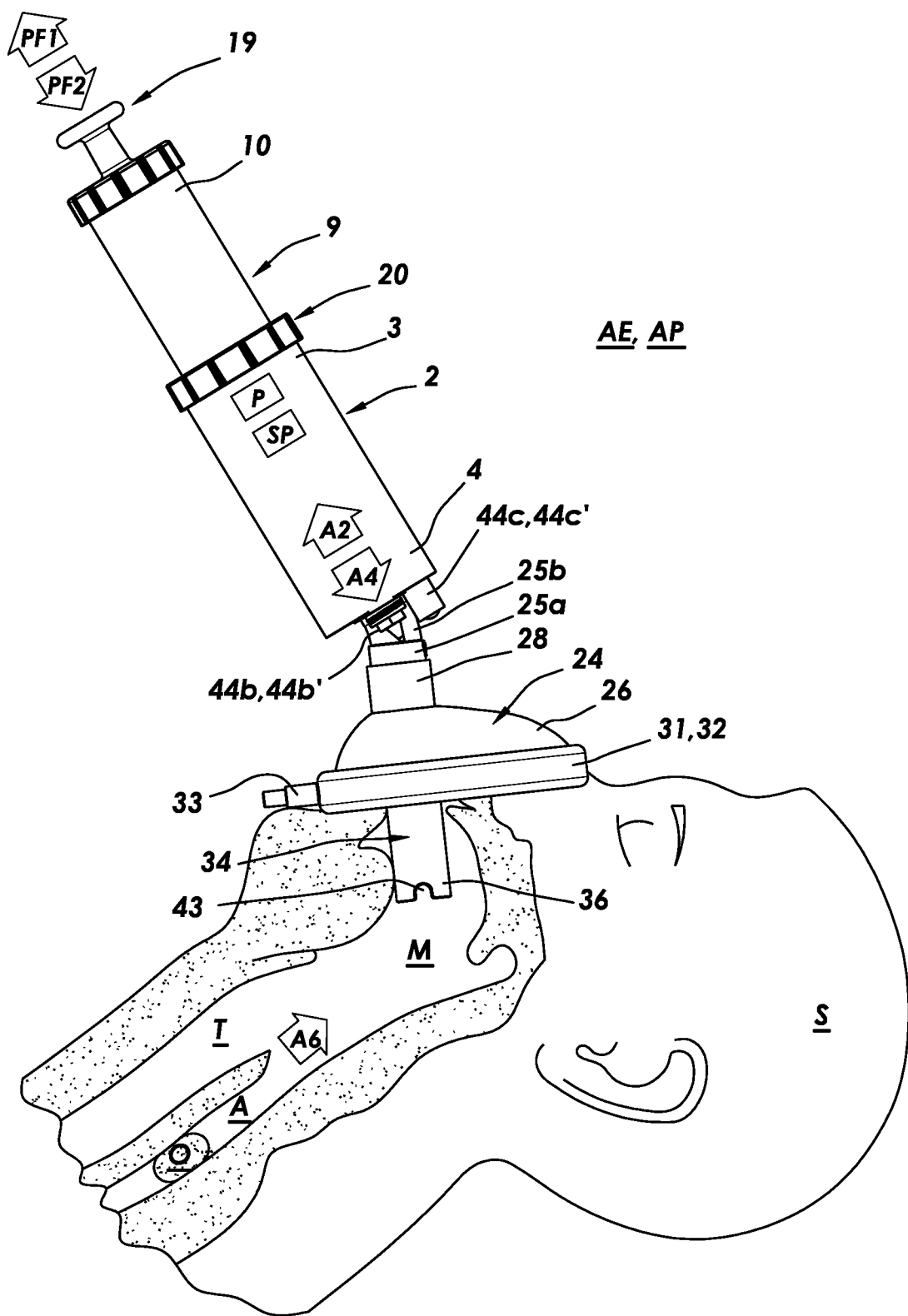
FIG. 8 illustrates a method of using a particular embodiment of the invention to dislodge an object from the throat.

Now with primary reference to FIGS. 2, 7 and 8, in particular embodiments, the annular cuff (31) can comprise an inflatable annular cuff (32). The inflatable annular cuff (32) can be inflated (depicted by arrow A1) to a firmness that allows the inflatable annular cuff (32) to conform to the subject's face (F) about the mouth (M) and nose (N). An inflatable annular cuff (32) can confer substantial advantages by engaging the subject's face (F) with a better fit or seal to retain the reduced pressure or suction generated during operation of the plunger (9) within the barrel (2), or to afford greater comfort to the subject (S). In particular embodiments, the inflatable annular cuff (32) can include a sealable fluid port (33) through which a fluid can ingress and egress the inflatable annular cuff (32) (depicted by arrow A1) to allow the firmness of the inflatable annular cuff (32) to be adjusted or to allow shipment in a deflated condition. In particular embodiments, the dome (26) can comprise a sufficiently transparent or clear material allowing observation of the subject (S) or the fluid or material (O) drawn up from a throat (T) of the subject (S) through the dome (26).

Again, with primary reference to FIGS. 7 and 8, a throat tube (34) having a length disposed between a throat tube first end (35) and a throat tube second end (36) can be coupled to or pass through the hollow stem (28) of the face mask (24) to directly, or indirectly through one or more hollow connectors (25), be fluidically coupled to the barrel distal end opening (5) in the barrel distal end (4) of the barrel (2). In the illustrative example of FIG. 7, the hollow stem (28) extending outward of the dome (26) of the face mask (24) can slidably engage a first portion (37) of a first hollow connector (25a). A second portion (38) of the first hollow connector (25a) having a lesser dimension passes through the hollow stem (28) and slidably receives the throat tube first end (35). The assembly of the first hollow connector (25a), the face mask (24), and the throat tube (34) can be fluidically connected to the barrel distal end opening (5) in the barrel distal end (4) directly or indirectly by a second hollow connector (25b) to fluidically couple the throat tube second end (36) to the barrel interior chamber (8). In particular embodiments, the first portion (37) of the first hollow connector (25a) can be configured to be removed from the barrel distal end (4). In particular embodiments, the first hollow connector (25a) can be removably friction fitted or threading mated to the tubular extension (30) surrounding the barrel distal end opening (5) in the barrel distal end (4) or to the second hollow connector (25b). As shown in the example of FIG. 7, the second hollow connector (25b) can include a radially extending pin (39) which can be slidingly received in a pin slot (40) in the first portion (37) of the first hollow connector (25a). The pin slot (40) can have an axial pin slot portion (41) and a transverse pin slot portion (42). The axial pin slot portion (41) in the first portion (37) of the first hollow connector (25a) can be aligned with the radially extending pin (39), the first portion (37) of the first hollow connector (25a) slidingly engaged with the second hollow connector (25b) to dispose the pin (39) in the axial pin slot portion (41). The first portion (37) of the first hollow connector (25a) can then be rotated to dispose the pin (39) in the transverse pin slot portion (42) to removably secure the first hollow connector (25a) to the second hollow connector (25b). In particular embodiments, the throat tube (34) can pass through the hollow stem (28) of the face mask (24) and directly, or indirectly through one or more hollow connectors (25) fluidically couple to the barrel distal end opening (5) at the barrel distal end (4) of the barrel (2). In particular embodiments, the hollow stem (28) and the throat tube (34) can be one piece.

Again, with primary reference to FIGS. 7 and 8, in particular embodiments, the throat tube (34) can, but need not necessarily, include one or more notches (43) at the throat tube second end (36). The one or more notches (43) can assist in preventing the tongue (T) of the subject (S) from be drawn by suction into the throat tube second end (36) during outward movement of the plunger (9) in the barrel (2). In particular embodiments, the throat tube (34) can curve approaching the tube second end (36) to assist in advancement of the throat tube (34) into the curvature of the airway (A). The throat tube (34) can comprise a rigid material; however, in certain embodiments can comprise resilient or pliant material, as examples: polyvinylchloride, polyethylene, polypropylene, polyurethane, rubber, silicone, or neoprene and combinations thereof.

Now, with primary reference to FIGS. 2, 3, 4A-4C, 5A-5D, embodiments can include one or more valves (44a, 44b, 44c) to regulate the pressure (P) in the barrel interior chamber (8) of the barrel (2) when the plunger (9) is pulled (PF1) toward the barrel proximal end (3) or the plunger (9) is pushed (PF2) toward the barrel distal end (4), and combinations thereof.

Figure 3:
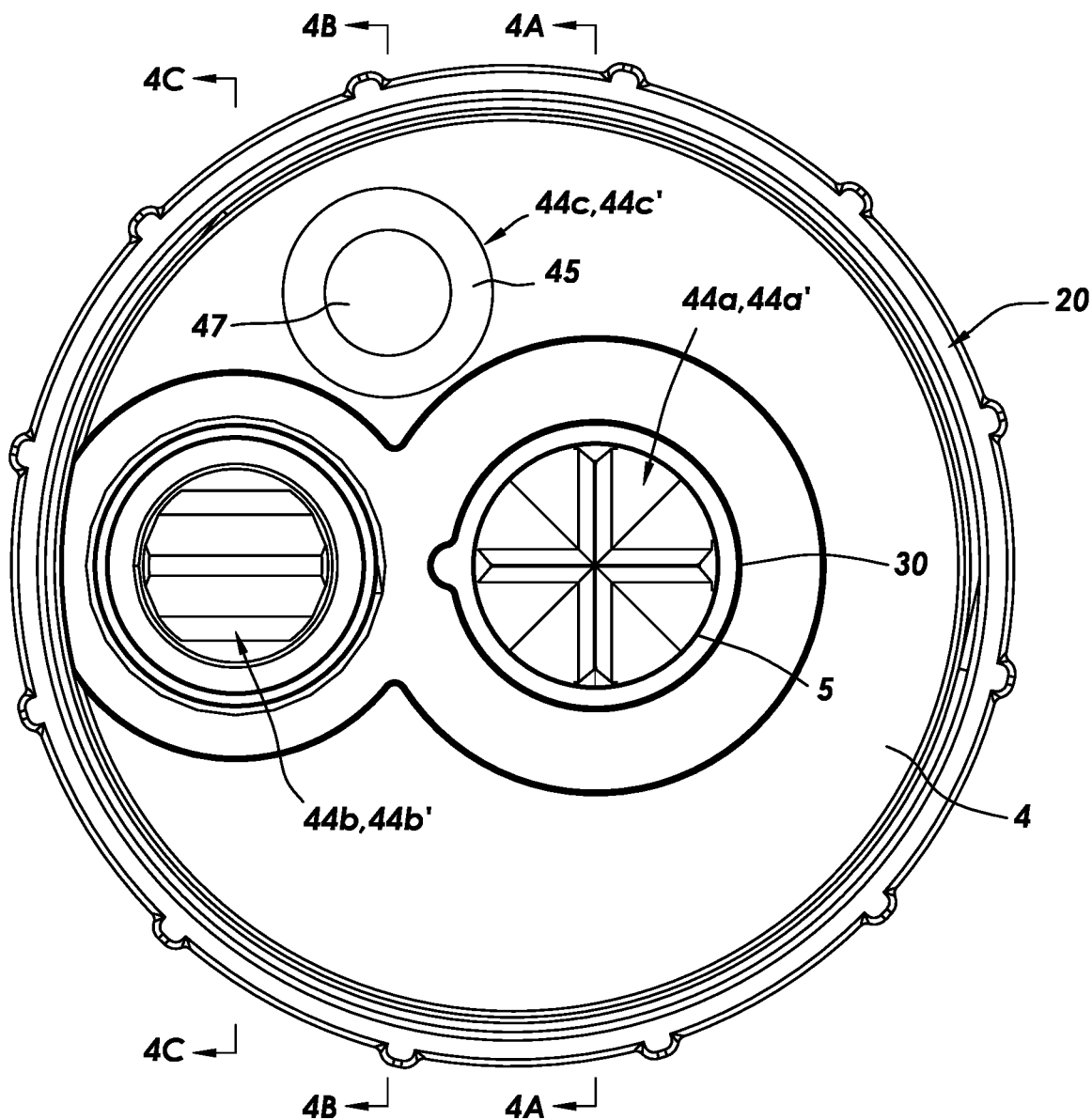
FIG. 3 is a cross section view 3-3 of the particular embodiment of the airway assist device as shown in FIG. 1D.
Figure 4C:
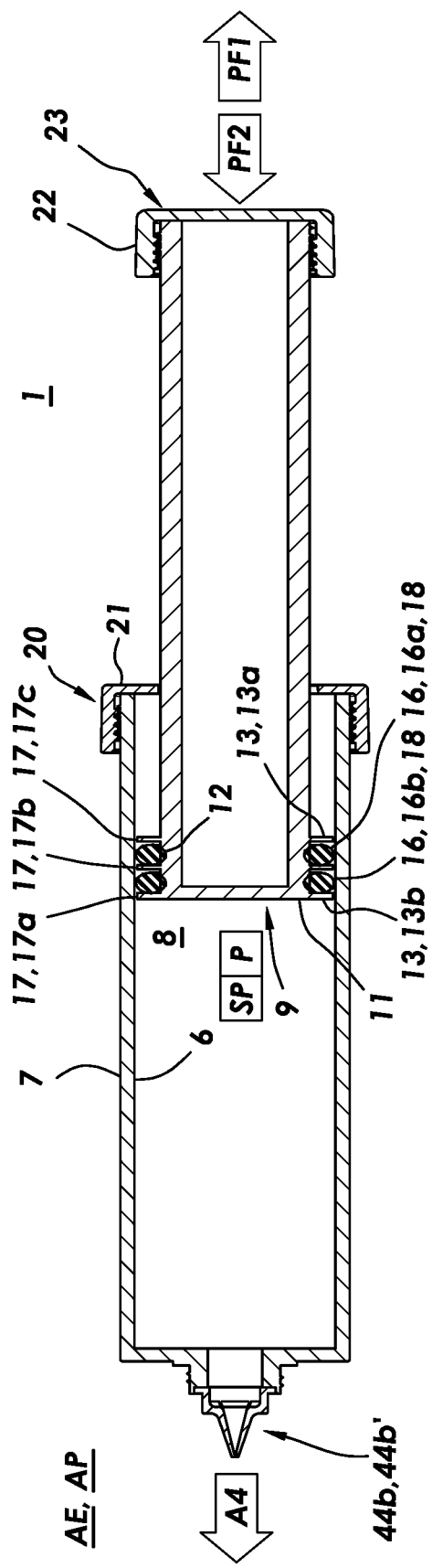
FIG. 4C is a cross section view 4C-4C of the particular embodiment of the airway assist device as shown in FIG. 3.
Figure 5A:
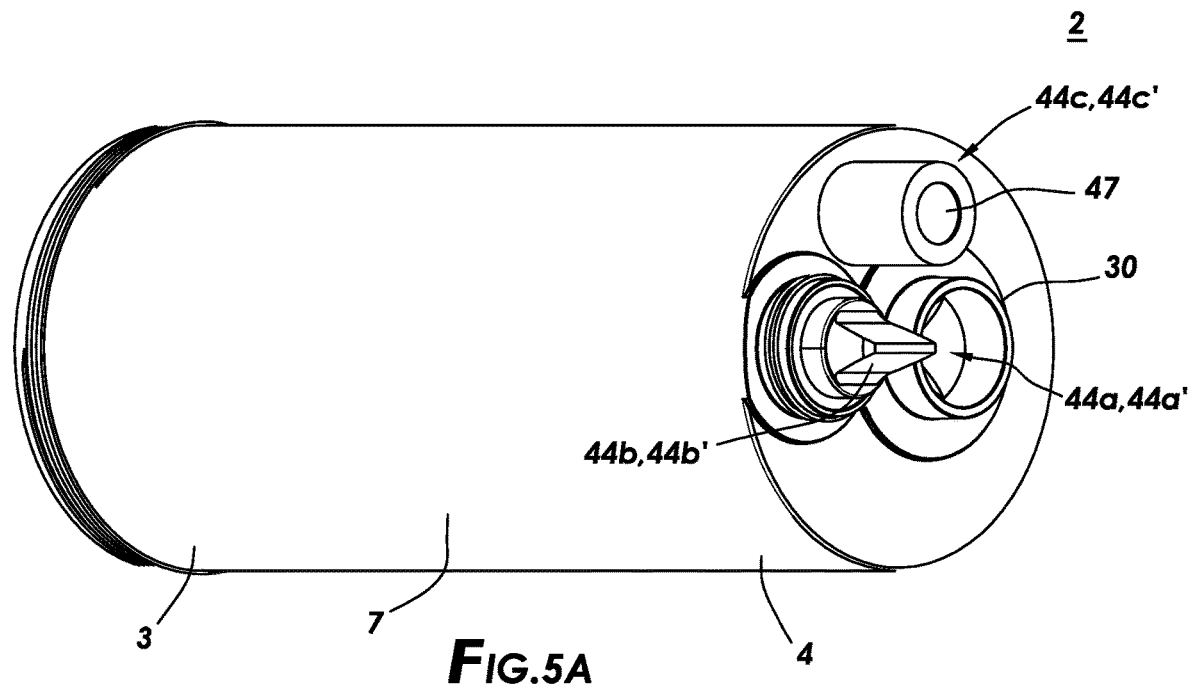
FIG. 5A is perspective second end view of the barrel and valve assembly of a particular embodiment of the airway assist device.
Figure 5B:
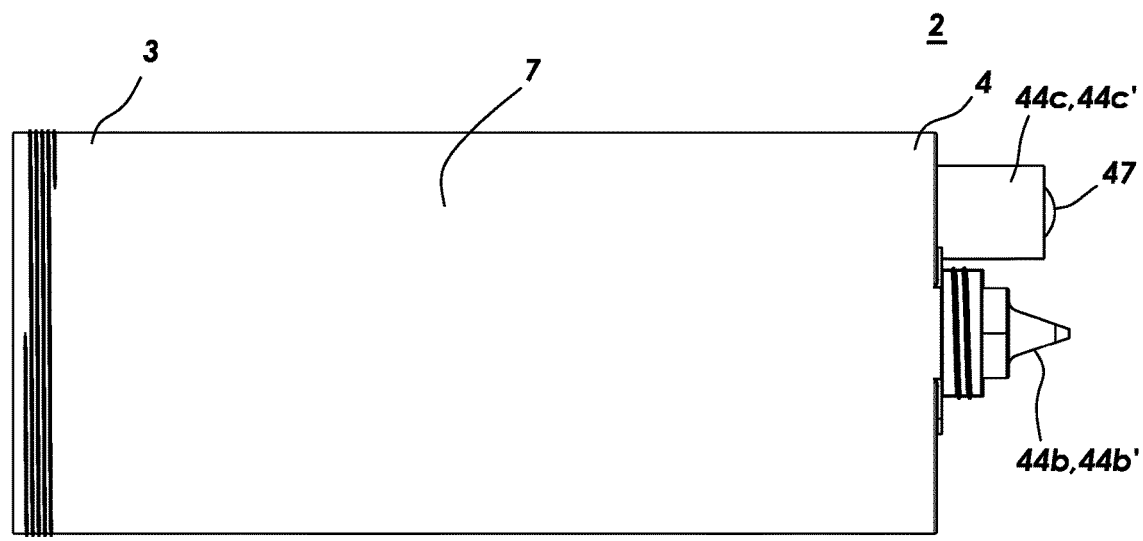
FIG. 5B is a first side elevation view of the barrel and valve assembly of a particular embodiment of the airway assist device.
Figure 6A:
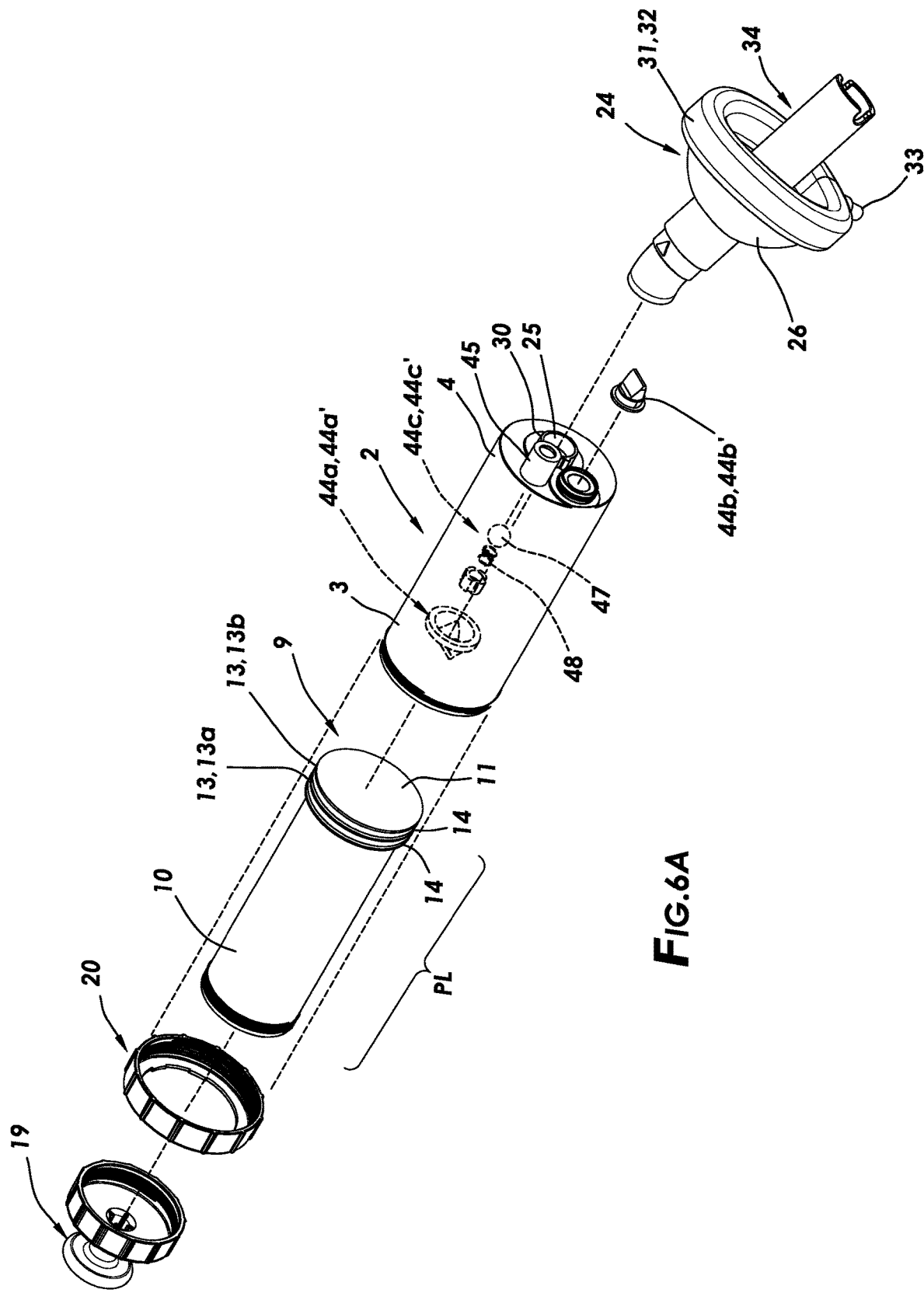
FIG. 6A is exploded perspective view of a particular embodiment of the airway assist device.
Figure 6B:
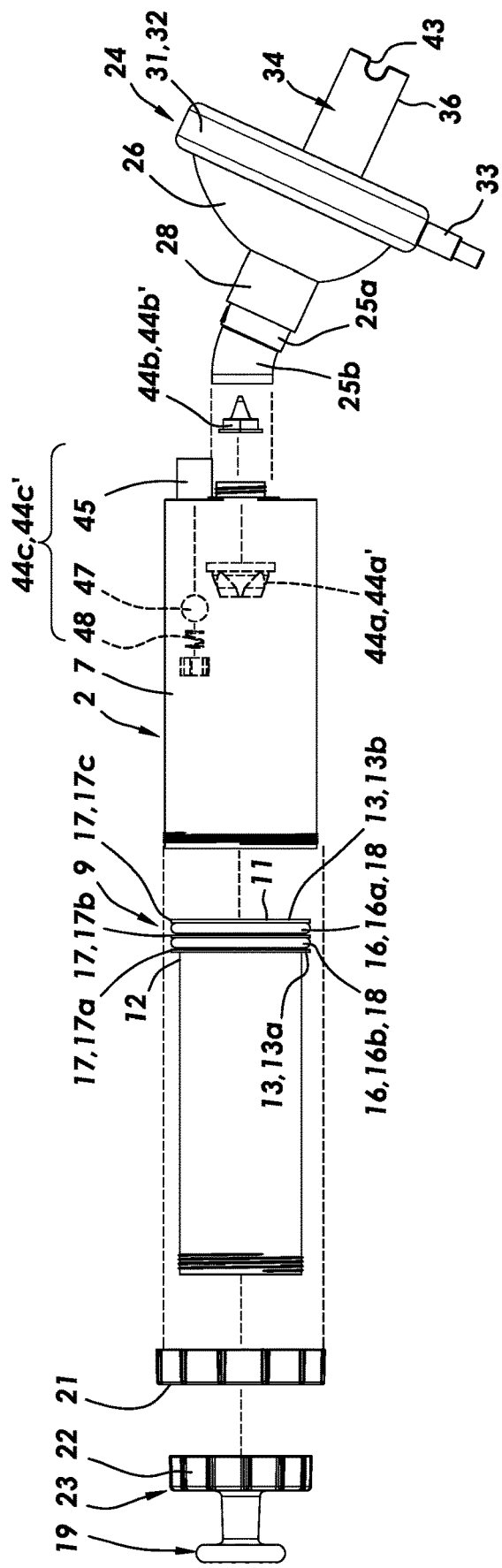
FIG. 6B is an exploded first side view of a particular embodiment of the airway assist device.

Now, with primary reference to FIGS. 3, 4A and 5D, particular embodiments can, but need not necessarily include, a one-way valve (44a) disposed to regulate fluid flow (depicted as arrow A2) through the barrel distal end opening (5) in the barrel distal end (4). There can be a substantial advantage in reducing or preventing fluid flow through the barrel distal end opening (5) in the barrel distal end (4) when the plunger (9) is pushed (PF2) toward the barrel distal end (4) (depicted as arrow A3) because the face mask (24) when engaged about the mouth (M) and nose (N) of the subject (S), can conduct the fluid flow into the throat (T) of the subject (S). The fluid flow (FF) can force the object (O) lodged in the throat (T) of the subject (S) even deeper into the throat (T) or can injure the lungs or force fluid into the veins or arteries of the lung (L). A one-way valve (44a) can be fluidically coupled to the barrel distal end opening (5) in the barrel distal end (4) (whether directly coupled in the barrel distal end opening (5) or coupled in the flow path to the face mask (24)) to prevent or substantially reduce fluid flow (FF) through the barrel distal opening (5) in the closed barrel distal end (4) upon inward push (PF2) of the plunger (9) toward the barrel distal end (4) of the barrel (2). As shown by the illustrative examples of FIGS. 3, 4A-4-C, and 5D, the one-way valve (44a) can be a cross-slit duckbill valve (44a') which allows fluid flow (FF) to pass into the barrel interior chamber (8) through the barrel distal end opening (5) in the barrel distal end (4) upon movement of the plunger (9) toward the barrel proximal end (3) of the barrel (2) (depicted as arrow A2), but prevents or substantially prevents fluid flow through the barrel distal end opening (5) in the barrel distal end (4) when the plunger (9) is pushed (PF2) toward the barrel distal end (4) (depicted as arrow A3). The illustrative example of a cross-slit duckbill valve (44a') is not intended to preclude embodiments in which the one-way valve (44a) has a structure other than a cross-slit duckbill valve (44a') but functions to allow fluid flow (FF) to pass into the barrel interior chamber (8) through the barrel distal end opening (5) in the barrel distal end (4) upon movement of the plunger (9) toward the barrel proximal end (3) (depicted as arrow A2), but prevents or substantially prevents fluid flow through the barrel distal end opening (5) in the barrel distal end (4) when the plunger (9) is pushed (PF2) toward the barrel distal end (4) (depicted as arrow A3). As further illustrative examples, depending on the embodiment, the one-way valve (44a) can comprise or consist of: a duck bill valve, an umbrella valve, a minivalveball valve, a dome valve, a belleville valve, a flapper valve, or a cross-slit valve, check valves, clack valves, non-return valves, reflux valves, retention valves, diaphragm valves, ball check valves, swing check valve, flapper valves, or combinations thereof.

Now, with primary reference to FIGS. 3, 4C and 5A-D, particular embodiments can, but not necessarily include, a one-way valve (44b) disposed to regulate fluid flow (depicted as arrow A4) from the barrel interior chamber (8) to the ambient environment (AE) when the plunger is pushed (PF2) toward the barrel distal end (4) (depicted as arrow A4). The one-way valve (44b) can be fluidically coupled to the barrel interior chamber (8) to allow fluid flow (FF) to pass through the one-way valve (44b) and out of the barrel interior chamber (8) to the ambient environment (AE) upon inward push (PF2) of the plunger (9) toward the barrel distal end (4) of the barrel (2). This can prevent or substantially reduces fluid flow (FF) through the barrel distal end opening (5) in the barrel distal end (4) of the barrel (2) when the plunger (9) is pushed (PF2) toward the barrel distal end (4). This can correspondingly prevent or substantially reduces the fluid flow (FF) through the barrel distal end opening (5) in the barrel distal end (4) and correspondingly to the face mask (24) or through the face mask (24) to the subject (S). This one-way valve (44b) can be used alone or in combination with the one-way valve (44a) fluidically coupled to the barrel distal end opening (5) in the barrel distal end (4) to corresponding prevent or substantially prevent fluid flow (FF) through the barrel distal end opening (5) in the barrel distal end (4) while allowing fluid flow (FF) to pass from the barrel interior chamber (8) to the ambient environment (AE). As shown by the illustrative examples of FIG. 3 and FIGS. 4A-4-C, the one-way valve (44b) can be a duckbill valve (44b') which allows fluid flow (FF) to pass from the barrel interior chamber (8) to the ambient environment (AE) upon movement of the plunger (9) toward the barrel distal end (4) and prevents or substantially prevents fluid flow (FF) through the duckbill valve (44b') upon movement of the plunger (9) toward the barrel proximal end (3). However, the illustrative example of a one-way valve (44b) being a duckbill valve (44b') is not intended to preclude embodiments in which the one-way valve (44b) has a structure other than a duckbill valve (44b') but functions to allow fluid flow (FF) to pass from the barrel interior chamber (8) to the ambient environment (AE) upon movement of the plunger (9) toward the barrel distal end (4), whether alone or in combination with the one-valve (44a) fluidically coupled to the barrel distal end opening (5) in the barrel distal end (4), prevents or substantially prevents fluid flow (FF) through the barrel distal end opening (5) in the barrel distal end (4), and functions to prevent fluid flow (FF) through the one-way valve (44b) from the ambient environment (AE) into the barrel interior chamber (8) upon movement of the plunger (9) toward the barrel proximal end (3). As further illustrative examples, depending on the embodiment, the one-way valve (44b) can comprise or consist of: a duck bill valve, an umbrella valve, a minivalveball valve, a dome valve, a belleville valve, a flapper valve, or a cross-slit valve, check valves, clack valves, non-return valves, reflux valves, retention valves, diaphragm valves, ball check valves, swing check valve, flapper valves, or combinations thereof.

Now, with primary reference to FIGS. 3, 4B, and 5A-5D, embodiments can include a one-way valve (44c) to regulate the pressure (P) in the barrel interior chamber (8) of the barrel (2) when the plunger (9) is pulled (PF1) toward the barrel proximal end (3). There can be a substantial advantage in regulating suction pressure (SP) generated in the barrel interior chamber (8) during movement of the plunger (9) toward the barrel proximal end (3) when the face mask (24) engages the subject (S) about the mouth (M) and nose (N). When the plunger (9) moves toward the barrel proximal end (3) and the face mask (24) engages the subject (S) about the mouth (M) and nose (N), the pressure (P) in the barrel interior chamber (8) can be substantially reduced. The reduction of pressure (P) in the barrel interior chamber (8) relative to the atmospheric pressure outside of the barrel (2) can be expressed as the numerical difference between the atmospheric pressure outside of the barrel (2) and the pressure (P) within the barrel interior chamber (8) in kilopascals (kPa) or millimeters of mercury (mmHg). Pressure (P) within the barrel interior chamber (8) less than atmospheric pressure are referred to herein as suction pressure (SP) expressed as positive values in kPa. As one example, if pressure (P) relative to atmospheric pressure is −10 kPa, the suction pressure (SP) can be expressed as a positive numerical value 10 kPa.

The substantial reduction in pressure (P) in the barrel interior chamber (8) can correspondingly be conducted to the throat (T) and lungs (L) of the subject (S). Negative-pressure pulmonary edema can develop whenever sub-atmospheric pressure (P) is generated at the alveolar level of the lungs (L). Accordingly, there would be an advantage in fluidically coupling a one-way valve (44c) to the barrel interior chamber (8) to allow suction pressure (SP) to develop in the barrel interior chamber (8) sufficient to dislodge an object (O) in the airway (A) or throat (T) of a subject (S), but not exceed a suction pressure (SP) that poses a risk of injury to the face (F), mouth (M), throat (T) or lungs (L) of the subject (S). As an illustrative example, there would be an advantage in an airway assist device (1) having a one-way valve (44c) that remained in the closed condition allowing suction pressure (SP) within the barrel interior chamber (8) to develop to a preselected kPa (mmHg) within the range of about 10 kPa (about 75 mm Hg) to about 60 kPa (465 mmHg) to assist in dislodging an object (O) in the throat (T) and transitioning to the open condition when the suction pressure (SP) within the barrel interior chamber (8) exceeds the preselected kPa to allow fluid flow (FF) from the ambient environment (AE) (shown by arrow A5) to enter the barrel interior chamber (8) to maintain or reduce suction pressure (SP) at or toward the preselected pKa (mmHg). The suction pressure (SP) at which the one-way valve transitions to the open condition can depend upon the condition of the subject (S). For example, injury due to sub-atmospheric pressure applied to the throat (T) or lungs (L) may vary based on factors such as age or health of the subject (S) or factors in the ambient environment (AE). Additionally, between jurisdictions there may differences in statutory law, rules, regulations, or other guidance on the suction pressure (SP) that can be applied by an airway assist device (1). Accordingly, the one-way valve (44c) can be differentially structured, interchanged, or provide adjustment, to accommodate a range of suction pressure (SP) suitable for use based on the differences between subjects (S) or jurisdictions to avoid or reduce prospective injury to the subject (S), including the face (F), mouth (L), throat (T), or lungs (L), or combinations thereof, due to suction pressure (SP) generated in the barrel interior chamber (8) and conducted to the face mask (24) engaged to the subject (S). Depending upon the embodiment, the one-way valve (44c) can be structured to open at a suction pressure (SP) of between about 10 kPa (about 75 mm Hg) to about 60 kPa (about 450 mm Hg). In particular embodiments, the one-way valve (44c) can be structured to open at a suction pressure (SP) selected from the group consisting of: about 11 kPa, about 12 kPa, about 13 kPa, about 14 kPa, about 15 kPa, about 16 kPa, about 17 kPa, about 18 kPa, about 19 kPa, about 20 kPa, about 21 kPa, about 22 kPa, about 22 kPa, about 23 kPa, about 24 kPa, about 25 kPa, about 26 kPa, about 27 kPa, about 28 kPa, about 29 kPa, about 30 kPa, about 31 kPa, about 32 kPa, about 33 kPa, about 34 kPa, about 35 kPa, about 36 kPa, about 37 kPa, about 38 kPa, about 39 kPa, about 40 kPa, about 41 kPa, about 42 kPa, about 43 kPa, about 44 kPa, about 45 kPa, about 46 kPa, about 47 kPa, about 48 kPa, about 49 kPa, about 50 kPa, about 51 kPa, about 52 kPa, about 53 kPa, about 54 kPa, about 55 kPa, about 56 kPa, about 57 kPa, about 58 kPa, and about 59 kPa, and combinations thereof. As shown in the illustrative examples of FIGS. 3 and 4B, in particular embodiments, the one-way valve (44c) can be structured as a ball check valve (44c') including a check valve seat (45) having a through-hole (46) fluidically coupled to the barrel interior chamber (8) and a ball (47) forcibly urged by a resilient member (48) against the check valve seat (45) to close the through-hole (46). In particular embodiments, the resilient member (48) can be a compression spring; however, this example is not intended to limit the resilient member to a compression spring and other resilient members can be used which urge the ball against the check valve seat (45) and can be compressed or resiliently bent. As the plunger (9) moves in the barrel (2) toward the barrel proximal end (3) the reduction of pressure (P) in the barrel interior chamber (8) relative to the atmospheric pressure outside of the barrel (2) acts on the ball (47) to compress the resilient member (48) and draw the ball (47) away from the through-hole (46) to open the ball check valve (44c') allowing fluid flow (FF) (typically atmospheric gases) to pass through the ball check valve (44c') into the barrel interior chamber (8). The fluid flow (FF) through the one-way valve (44c) can prevent, slow, or reverse reduction in pressure (P) or maintain a pressure (P) within the barrel interior chamber (8) relative the atmospheric pressure. In particular embodiments, the one-way valve (44c) can maintain suction pressure (SP) at preselected suction pressure (SP), or reduce suction pressure (SP) toward a preselected suction pressure (SP) within the barrel chamber (8) relative to atmospheric pressure outside the barrel (2). The one-way valve (44c) can be used alone or in combination with one or more of a one-way valve (44a) which regulates fluid flow (FF) through the barrel distal end opening (5) in the barrel distal end (4) when the plunger (9) is pushed (PF2) toward the barrel distal end (4) (depicted by arrow A3), or one-way valve (44b) disposed to regulate fluid flow (FF) from the barrel interior chamber (8) to the ambient environment (AE) when the plunger (9) is pushed (PF2) toward the barrel distal end (4) (depicted as arrow A4). As shown in the illustrative examples depicted in the Figures, embodiments can include all of the one-way valves (44a, 44b, 44c) as above described; however, this is not intended to preclude embodiments which include only one of the three one-way valves (44a, 44b, or 44c) above described, combinations of two of the three one-way valves (44a and 44b) (44a and 44c) (44b and 44c) above described, or all three of the one-way valves (44a, 44b and 44c) above described.

Now with primary reference to FIG. 8, a method of using embodiments of the airway assist device (1) can comprise, consist essentially of or consist of one or more of: slidably engaging the plunger (9) in the barrel (2) (depicted by arrows PF1 and PF2). The plunger (9) can be pushed (PF2) inwardly in the barrel (2) toward the barrel distal end (4) until the plunger distal end (11) has a location proximate to or engages or abuts the barrel distal end (4) of the barrel (2). With the face mask (24) fluidically coupled to the barrel interior chamber (8), the method can further comprise inserting the throat tube (34) into the throat (T) of the subject (S). Curved or flexible throat tubes (34) can allow embodiments of the throat tube (34) to be inserted more readily in the curvature of the mouth (M) and throat (T) of the subject (S). The method can further comprise engaging the face mask (24) about the mouth (M) and nose (N) of the subject (S). The throat tube (34) can be dimensioned such that once the face mask (24) engages the face (F) of the subject (S), the throat tube second end (36) has the proper location in the throat (T). Accordingly, the configuration of the mask (24) in relation to the configuration of the throat tube (T) acts as a stop and prevents over insertion of the throat tube (34) into the throat (T) which can cause the fluid or other material (O) to be pushed deeper into the subject's airway (A).

Upon proper positioning of the throat tube (34) within the person's throat (T), the method can further comprise outwardly drawing the plunger (9) slidably disposed within the barrel (2) (depicted by arrow PF1) to generate a suction pressure (SP) in the throat tube (34) which causes air to be drawn into the throat tube second end (36)(depicted by arrow A2). The air drawn into the throat tube second end (36) assists in dislodging, expelling or drawing the fluid or other material (O) up and out of the throat (T) (depicted by arrow A6). A retainer ring (20) can prevent the plunger (9) from being removed from within the barrel (2). The transparent material of the dome (26) of the face mask (24) can allow the subject (S) or fluids and materials (O) to be observed through the dome (26). As one example, if the subject (S) has vomited or if fluid or material (O) has been transferred to the barrel interior chamber (8) of the barrel (2), the method can then further comprise removing the throat tube (34) from the throat (T) of the subject (S). The method can then further comprise inwardly pushing the plunger (9) in said barrel (2) (PF2) to generate a positive pressure in the barrel interior chamber (9) and expelling the fluid or material (O) from said barrel interior chamber (8) through the one-way valve (44b) (depicted by arrow A4). The method can be repeated with or without removal of throat tube from the throat (T).

As can be easily understood from the foregoing, the basic concepts of the present invention may be embodied in a variety of ways. The invention involves numerous and varied embodiments of an airway assist device (1) and methods for making and using such airway assist device (1) including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "connector" should be understood to encompass disclosure of the act of "connecting"—whether explicitly discussed or not—and, conversely, were there is a disclosure of the act of "connecting", such a disclosure should be understood to encompass disclosure of a "connector" and even a "means for connecting". Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Further, for the purposes of the present invention, the term "coupled" or derivatives thereof can mean indirectly coupled, coupled, directly coupled, connected, directly connected, or integrated with, depending upon the embodiment.

Additionally, for the purposes of the present invention, the term "integrated" when referring to two or more components means that the components (i) can be united to provide a one-piece construct, a monolithic construct, or a unified whole, or (ii) can be formed as a one-piece construct, a monolithic construct, or a unified whole. Said another way, the components can be integrally formed, meaning connected together so as to make up a single complete piece or unit, or so as to work together as a single complete piece or unit, and so as to be incapable of being easily dismantled without destroying the integrity of the piece or unit.

Thus, the applicant(s) should be understood to claim at least: i) each of the airway assist device herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application, if any, provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon. The elements following an open transitional phrase such as "comprising" may in the alternative be claimed with a closed transitional phrase such as "consisting essentially of" or "consisting of" whether or not explicitly indicated the description portion of the specification.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. An airway assist device, comprising:
   a barrel having a barrel proximal end and a barrel distal end, said barrel distal end having a first barrel distal end opening;
   a plunger slidably disposed within said barrel;
   a face mask having a hollow stem fluidically coupled to said first barrel distal end opening at said barrel distal end, said face mask configured to seal about a mouth and nose of a person; and
   a first one-way valve coupled to a second barrel distal end opening at said barrel distal end through which fluid passes into said barrel, said first one-way valve configured to regulate suction pressure within said barrel upon outward draw of said plunger in said barrel toward said barrel proximal end, said first one-way valve opens at a preselected suction pressure relative to atmospheric pressure outside of said barrel.

2. The airway assist device of claim 1, wherein said first one-way valve opens to regulate said suction pressure within said barrel relative to said atmospheric pressure outside of said barrel at about 10 kPa to about 60 kPa.

3. The airway assist device of claim 1, wherein said first one-way valve coupled to said barrel comprises a ball check valve including a check valve seat having a through-hole fluidically coupled to said second barrel distal end opening at said barrel distal end and a ball forcibly urged by a resilient member against said check valve seat to close said through-hole.

4. The airway assist device of claim 3, wherein reduced pressure in said barrel draws said ball away from said through-hole to allow fluid to pass through said second barrel distal end opening into said barrel.

5. The airway assist device of claim 1, further comprising a second one-way valve coupled to said first barrel distal end opening at said barrel distal end through which fluid passes into said barrel upon outward draw of said plunger in said barrel.

6. The airway assist device of claim 5, further comprising a third one one-way valve coupled to a third barrel distal end opening in said barrel distal end through which fluid passes out of said barrel upon inward push of said plunger in said barrel.

7. The airway assist device of claim 1, further comprising a first channel encircling said plunger; and
   a first seal disposed in said first channel and encircling said plunger.

8. The airway assist device of claim 7, further comprising:
   a second channel encircling said plunger; and
   a second seal disposed in said second channel and encircling said plunger.

9. The airway assist device of claim 8, wherein said first channel adjacent said second channel.

10. The airway assist device of claim 1, further comprising a tubular connector having a connector first end coupled to said first barrel distal end opening at said barrel distal end and a connector second end coupled to said face mask.

11. The airway assist device of claim 10, wherein said tubular connector having a non-straight angle between said connector first end and said connector second end.

12. The airway assist device of claim 1, wherein said face mask has a dome extending to a dome outer periphery configured to seal about a mouth and nose of a person.

13. The airway assist device of claim 12, wherein said dome comprises a clear material allowing a user to observe a person engaged to said face mask or a material drawn up from a throat of said person.

14. The airway assist device of claim 13, wherein said dome outer periphery is engaged to an annular cuff configured to seal about a mouth and nose of a person.

15. The airway assist device of claim 14, wherein said annular cuff comprises an inflatable tubular member having a sealable fluid port through which fluid ingresses or egresses said annular cuff.

16. The airway assist device of claim 1, wherein said face mask removably couples to said first barrel distal end opening at said barrel distal end to allow a plurality of face masks to interchangeably couple to said first opening.

17. The airway assist device of claim 16, wherein said plurality of face masks include a range of different sizes configured to correspondingly seal about a mouth and nose of a plurality of persons having different size.

18. The airway assist device of claim 1, further comprising a throat tube passing through said face mask, said throat tube having a tube first end fluidically connected to said first barrel distal end opening at said barrel distal end and a tube second end configured to insert into a throat of said person.

19. The airway assist device of claim 1, wherein said plunger comprises a hollow tube having three concentric rings encircling an outer surface of said hollow tube, said three concentric rings disposed in spaced apart relation to form a first channel and a second channels.

20. The airway assist device of claim 19, further comprising a retainer ring having an inwardly extending retainer ring shoulder coupled to said barrel proximal end, wherein a proximal one of said three concentric rings engages said retainer ring shoulder to prevent said plunger from withdrawal from said barrel proximal end.

21. The airway assist device of claim 1, further comprising a handle connected to said plunger and extending outward of said barrel proximal end.

22. The airway assist device of claim 19, further comprising a handle connected to said plunger and extending outward of said barrel proximal end.

* * * * *